United States Patent [19]
Kobrehel et al.

[11] 3,983,103
[45] Sept. 28, 1976

[54] N-(BENZENESULFONYL)-ERYTHROMYCYLAMINE DERIVATIVES

[75] Inventors: Gabrijela Kobrehel; Zrinka Tamburašev; Slobodan Djokić, all of Zagreb, Yugoslavia

[73] Assignee: PLIVA Pharmaceutical and Chemical Works, Zagreb, Yugoslavia

[22] Filed: July 14, 1975

[21] Appl. No.: 595,593

Related U.S. Application Data

[63] Continuation-in-part of Ser. No. 434,243, Jan. 17, 1974, abandoned.

[30] Foreign Application Priority Data
Jan. 19, 1973 Yugoslavia............................ 151/73

[52] U.S. Cl....................................... 536/9; 424/180
[51] Int. Cl.².......................................... C07H 15/20
[58] Field of Search .................................. 260/210 E

[56] References Cited
UNITED STATES PATENTS
3,869,444   5/1975   Freiberg.......................... 260/210 E

*Primary Examiner*—Johnnie R. Brown
*Assistant Examiner*—Cary Owens
*Attorney, Agent, or Firm*—Kurt Kelman

[57] ABSTRACT

The new antibiotic compounds N-(4-R-benzenesulfonyl)-erythromycylamine, wherein R is a lower alkyl group having 1–5 carbon atoms, an acylamino group wherein the acyl has 2–4 carbon atoms, or a halo group.

7 Claims, No Drawings

N-(BENZENESULFONYL)-ERYTHROMYCYLAMINE DERIVATIVES

The present application is a continuation-in-part of our copending application Ser. No. 434,243, filed Jan. 17, 1974, now abandoned.

The present invention relates to new antibiotic compounds, and more particularly to N-(4-R-benzenesulfonyl)erythromycylamines, wherein R is a lower alkyl group having 1–5 carbon atoms, an acylamino group wherein the acyl has 2–4 carbon atoms, or a halo group represented by a chlorine, bromine, iodine or fluorine atom.

The novel compounds are represented by the following formula:

These derivatives may be prepared by the reaction of erythromycylamine with para-substituted benzenesulfochlorides of the formula $R-SO_2Cl$, wherein R is selected from the above-defined groups. This reaction is effected in an inert solvent, such as acetone or benzene, in the presence of two to four moles of an alkaline metal salt, such as sodium hydrogen carbonate or sodium carbonate. One to two moles of the sulfochloride are used per mole of the erythromycylamine, and the reaction proceeds at an elevate temperature. The derivatives of this invention may be recovered from the reaction mixture by conventional methods.

All of the novel compounds hereinabove defined have shown impressive antibiotic activity against gram-positive and gram-negative microorganisms, as exemplified by the following Table:

TABLE I

| | MIC in mcg/ml of erythromycin and its derivatives | | | | | |
|---|---|---|---|---|---|---|
| Organisms | E | EA | EAT | EAAc | EACl | EABr |
| E. coli | 250 | 250 | 62.2 | 15 6 | 62.5 | 125.0 |
| Pseudomonas aeruginosa | 500 | 500 | 250.0 | 250.0 | 250.0 | 250.0 |
| Klebsiella aerogenes | 500 | 500 | 250 | 62.5 | 125 | 62.5 |
| Streptococcus haemolyticus | 31.2 | 31.2 | 0.9 | 0.45 | 0.9 | 0.9 |
| Staphylococcus pyog. aureus | 62.5 | 250 | 31.2 | 15.6 | 31.2 | 31.2 |
| Enterococcus | 31.2 | 31.2 | 3.9 | 1.9 | 3.9 | 1.9 |
| Diplococcus pneumoniae | 62.5 | 62.5 | 1.9 | 1.9 | 1.9 | 3.9 |
| Proteus mirabilis | 500 | 250 | 250 | 125 | 250 | 250 |

TABLE II

| | MIC in mcg/ml of erythromycin and its derivatives | | | | | | | | | |
|---|---|---|---|---|---|---|---|---|---|---|
| Organisms | EA | EAT | o-EAT | EAE | EAF | EACl | EABr | EAI | EAAc | EAPr |
| Streptococcus haemolyticus 69 | 0.9 | 0.9 | 0.9 | 0.9 | 3.9 | 0.9 | 0.9 | 0.9 | 0.9 | 0.9 |
| Streptococcus haemolyticus 099 | 0.9 | 0.9 | 1.9 | 0.9 | <0.9 | 0.9 | 0.9 | 0.9 | 1.9 | 0.9 |
| Staphylococcus aureus 736 | 1.9 | 15.6 | 31.2 | 31.2 | 31.2 | 31.2 | 7.8 | 15.6 | 31.2 | 15.6 |
| Staphylococcus aureus 372 | <0.9 | 7.8 | 15.6 | 7.8 | 15.6 | 3.9 | 3.9 | 3.9 | 15.6 | 15.6 |
| Enterococcus 45 | 7.8 | 7.8 | 7.8 | 7.8 | 7.8 | 3.9 | 7.8 | 7.8 | 125.0 | 62.5 |
| Enterococcus 242 | 0.9 | 3.9 | 3.9 | 3.9 | 3.9 | 3.9 | 3.9 | 7.8 | 62.5 | 31.2 |
| Enterococcus 146 | 0.9 | 7.8 | 15.6 | 7.8 | 7.8 | 7.8 | 3.9 | 3.9 | 31.2 | 7.8 |
| Enterococcus 325 | 250.0 | 7.8 | 7.8 | 3.9 | 7.8 | 7.8 | 3.9 | 3.9 | 62.5 | 62.5 |

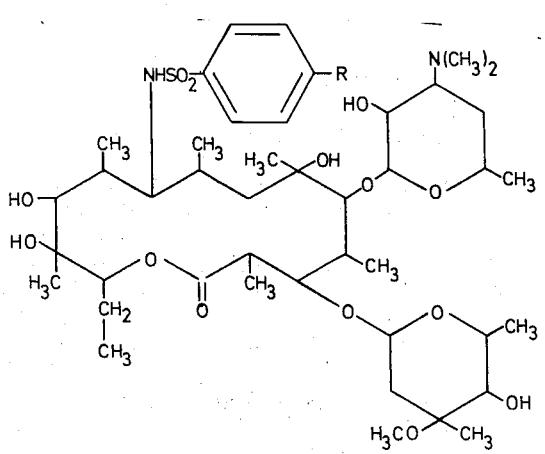

E = erythromycin
EA = erythromycylamine
O-EAT = N-(Z-methyl-benzensulfonyl)EA
EAT = N-(4-methyl-benzenesulfonyl) EA
EAAc = N-(4-acetyl-benzenesulfonyl)EA
EACl = N-(4-chloro-benzenesulfonyl)EA
EABr = N-(4-bromo-benzenesulfonyl) EA
EAI = N-(4-iodo-benzenesulfonyl) EA
EAF = N-(4-fluoro-benzenesulfonyl) EA
EAE = N-(4-ethyl-benzenesulfonyl) EA
EAPr = N-(4-propionyl-benzenesulfonyl) EA The above Table I illustrates antibacterial spectrum in vitro, using some pathogene microorganisms freshly isolated from patients. Table II shows the results obtained in testing further compounds for their resistance against a set of organisms.

Table III illustrates extraordinary synergism when the novel derivatives of the invention are used in combination with trimetoprim (2,4-diamino-5-(3', 4', 5'-trimethoxybenzyl)-pyrimidine), designated T.

Analysis for $C_{43}H_{73}N_2O_{14}ClS$ Calculated S 3.54%; Found S 3.21%

TABLE III

|  | MIC in mcg/ml | | | | | | | | | | |
|---|---|---|---|---|---|---|---|---|---|---|---|
|  | E + T | | EA + T | | EAT + T | | EAAc + T | | EACl + T | | EABr + T | |
| E. coli | 125 | 6.3 | 250 | 12.5 | 7.8 | 0.4 | 3.8 | 0.2 | 15.6 | 0.8 | 31.2 | 1.7 |
| Pseudomonas aeruginoza | 125 | 6.3 | 125 | 6.3 | 62.2 | 3.2 | 31.2 | 1.7 | 62.2 | 3.2 | 62.2 | 3.2 |
| Klebsiella aerogenes | 125 | 6.3 | 125 | 6.3 | 62.2 | 3.2 | 15.6 | 0.8 | 62.2 | 3.2 | 62.2 | 3.2 |
| Streptococcus haemolyticus | 7.8 | 0.4 | 7.8 | 0.4 | 0.45 | 0.025 | 0.45 | 0.025 | 0.45 | 0.025 | 0.45 | 0.025 |
| Staphylococcus pyog. aureus | 62.2 | 3.2 | 62.2 | 3.2 | 3.8 | 0.2 | 1.8 | 0.1 | 7.8 | 0.4 | 15.6 | 0.8 |
| Enterococcus | 7.8 | 0.4 | 7.8 | 0.4 | 0.45 | 0.025 | 0.45 | 0.025 | 0.45 | 0.025 | 0.45 | 0.025 |
| Diplococcus pneumoniae | 31.1 | 1.7 | 31.1 | 1.7 | 0.45 | 0.025 | 0.45 | 0.025 | 0.45 | 0.025 | 0.45 | 0.025 |
| Proteus mirabilis | 125 | 6.3 | 125 | 6.3 | 62.2 | 3.2 | 15.6 | 0.8 | 62.2 | 3.2 | 62.2 | 3.2 |

The following examples illustrate the practice of the present invention.

EXAMPLE 1

N-(4-methyl-benzenesulfonyl)erythromycylamine

A solution of 0.78 grams (0.00408 mole) p-toluenesulfochloride in 30 ml benzene was dropwise added to a solution of 3 grams (0.00408 mole) erythromycylamine in 90 ml of benzene under stirring over a period of one hour. At the same time, a solution of 1.8 grams (0.01632 mole) of sodium hydrogen carbonate in 30 ml water was added dropwise. The stirring was continued for an additional 4 hours while heating the reaction mixture at 50°C. After cooling to room temperature, 45 ml. of 0.1 N NaOH was added and stirring was continued for 2 hours.

The two layers which formed were separated, and a benzene layer was washed with 10% NaHCO₃ and dried over CaCl₂. Benzene was evaporated under vacuum, and N-(4-methyl-benzenesulfonyl)erythromycylamine was obtained. The recovered product was found to have the following values:
M. P. 136°–139°C
Analysis for $C_{44}H_{76}N_2O_{14}S$: Calculated - S 3.61%; Found - S 3.25%
$[\alpha]_D^{20} = -41°$ (1%, CHCl₃)

EXAMPLE 2

N-(4-chloro-benzenesulfonyl)erythromycylamine

A solution of 3 grams (0.00408 mole) erythromycylamine in 100 ml acetone and 0.687 grams (0.00816 mole) of NaHCO₃ in 30 ml H₂O were added dropwise to a solution of 0.861 grams (0.00408 mole) p-chlorobenzenesulfonylchloride in 30 ml acetone under stirring over a period of one hour at room temperature. The reaction mixture was then refluxed for 4 hours, and after cooling to room temperature (pH 8.7) was evaporated under vacuum. The water suspension which remained was extracted once with 100 ml and twice each with 50 ml portions of methylenechloride at pH 6 (pH was adjusted with 1 N HCl). The combined extracts were washed with 50 ml of saturated NaHCO₃ solution, and 50 ml of water, and dried with K₂CO₃. The methylenechloride was evaporated under vacuum, and N-(4-chloro-benzenesulfonyl)erythromycylamine was obtained. The recovered product was found to have the following values:
M. P. 161°–169°C
$[\alpha]_D^{20} = 37°$ (1% in CHCl₃)

EXAMPLE 3

N-(4-acetylamino-benzenesulfonyl)erythromycylamine 1.92 grams (0.00816 mole) of p-acetylaminobenzenesulfochloride was dissolved in 80 ml acetone - water mixture (1:1). A solution of 3 grams (0.00408 mole) erythromycylamine in 100 ml acetone and 1 gram (0.0119 mole) of NaHCO₃ dissolved in 60 ml water was added dropwise to this solution under stirring conditions for a period of one hour. After this addition was completed, the reaction mixture was refluxed for 8 hours, cooled to room temperature, and was then evaporated under vacuum. From the remaining water suspension, a pure substance was obtained by the procedure described in Example 2. The recovered product was found to have the following values:
M. P. 171°–176°C
Analysis for $C_{45}H_{77}N_3O_{15}S$; Calculated S 3.44%; Found S 3.93%
$[\alpha]_D^{20} = -32°$ (1% in CHCl₃)

EXAMPLE 4

N-(4-acetylamino-benzenesulfonyl)erythromycylamine

A solution of 1.92 grams (0.00816 mole) of p-acetylaminobenzenesulfonylchloride in 40 ml acetone and 1.80 grams (0.01632 mole) of sodium carbonate in 30 ml water were added dropwise to a solution of 3 grams (0.00408 mole) of erythromycylamine in 90 ml benzene, with stirring over a period of one hour at room temperature. After this addition was completed, the reaction mixture was heated to 50°C, stirred for two hours, cooled to room temperature and then stirred for an additional 4 hours (pH of the reaction mixture being 9.6). The two layers which formed were separated, the benzene layer washed three times with 40 ml portions of water and then dried with calcium chloride. Benzene was removed and pure N-(4-acetylamino-benzenesulfonyl)erythromycylamine was obtained. The recovered product was found to have the following values:
M. P. 171°–176°C
Analysis for $C_{45}H_{77}N_3O_{15}S$; Calculated S 3.44%; Found S 3.50%
$[\alpha]_D^{20} = -32°$ (1% in CHCl₃)

EXAMPLE 5

N-(4-bromo-benzenesulfonyl)erythromycylamine

A solution of 1.044 grams (0.00408 mole) p-bromobenzenesulfonylchloride in 60 ml acetone and 0.525 gram (0.00624 mole) of sodium hydrogen carbonate in 30 ml water was added dropwise to a solution of 3 grams (0.00408 mole) of erythromycylamine in 100 ml acetone with stirring over a period of one hour at room temperature. After this addition was completed, the reaction mixture was refluxed for 6 hours, cooled to room temperature and stirred for additional 6 hours (pH of the reaction mixture being 10.1). Acetone was removed by evaporation under vacuum and the remaining water suspension was extracted three times with 50 ml portions of dichloromethane after adjusting pH with 1 N hydrochloric acid to 6. The combined dichloromethane extracts were washed with 50 ml of a saturated $NaHCO_3$ solution and then with 50 ml of water and dried with potassium carbonate.

The solvent was removed under vacuum and pure N-(4-bromo-benzenesulfonyl) erythromycylamine was obtained. The recovered product was found to have the following values:

M. P. 157°–159°C

Analysis for $C_{43}H_{73}N_2O_{14}BrS$; Calculated S 3.36 %; Found S 3.62 %

$[\alpha]_D^{20} = -35.93°$ (1% in $CHCl_3$)

EXAMPLE 6

N-(4-iodo-benzenesulfonyl)erythromycylamine

A solution of 1.236 grams (0.00408 mole) p-iodo-benzenesulfonylchloride in 40 ml acetone and 0.525 gram (0.00624 mole) sodium hydrogen carbonate in 30 ml water were added dropwise to a solution of 3 grams (0.00408 mole) erythromycylamine in 90 ml acetone with stirring over a period of one hour at room temperature. After this addition was completed, the reaction mixture was refluxed for 6 hours, then cooled to room temperature (pH of the mixture being 11.25). Acetone was removed by evaporation under vacuum and the remaining water suspension was extracted three times with 50 ml portions of dichloromethane after adjusting pH with 1 N hydrochloric acid to 6. The combined dichlorolmethane extracts were washed with 50 ml of a saturated $NaHCO_3$ solution and then with 50 ml of water and dried with potassium carbonate. The solvent was removed under vacuum and pure N-(4-iodo-benzenesulfonyl)erythromycylamine was obtained. The recovered product was found to have the following values:

M. P. 169°–175°C

Analysis for $C_{43}H_{73}N_2O_{14}IS$: Calculated S 3.23%; Found S 3.61%

$[\alpha]_D^{20} = -35.67°$ (1% in $CHCl_3$)

EXAMPLE 7

N-(4-fluoro-benzenesulfonyl)erythromycylamine

A solution of 0.795 gram (0.00408 mole) p-fluorobenzenesulfonylchloride in 40 ml acetone and 0.525 gram (0.00624 mole) sodium hydrogen carbonate in 30 ml water were added dropwise to a solution of 3 grams (0.00408 mole) erythromycylamine in 90 ml acetone with stirring over a period of one hour at room temperature. After this addition was completed, the reaction mixture was refluxed for 3 hours, cooled to room temperature and stirred for additional 4 hours (pH of the reaction mixture being 9.1). Acetone was removed by evaporation under vacuum and the remaining water suspension was extracted 3 times with 50 ml portions of dichloromethane after adjusting pH with 1 N HCl to 6. The combined dichloromethane extracts were washed with 50 ml of a saturated $NaHCO_3$ solution and then with 50 ml of water and dried with potassium carbonate. The solvent was evaporated under vacuum and pure N-(4-fluoro-benzenesulfonyl) erythromycylamine was obtained. The recovered product was found to have the following values:

M. P. 158°–163°C

Analysis for $C_{43}H_{73}N_2O_{14}FS$: Calculated S 3.59%; Found S 3.22%

$[\alpha]_D^{20} = -38.28°$ (1% in $CHCl_3$)

EXAMPLE 8

N-(4-ethyl-benzenesulfonyl)erythromycylamine

A solution of 0.84 gram (0.00408 mole) p-ethylbenzenesulfonylchloride in 30 ml benzene and 1.80 grams (0.0163 mole) of sodium carbonate in 30 ml water were added dropwise to a solution of 3 grams (0.00408 mole) erythromycylamine in 90 ml benzene under stirring over a period of one hour at room temperature. After this addition was completed, the reaction mixture was heated to 50°C, stirred for 5 hours, cooled to room temperature and then stirred for additional 4 hours (pH of the reaction mixture being 9.6). The two layers which formed were separated and the benzene layer was washed 3 times with 30 ml portions of water and then dried with calcium chloride. Benzene was removed and pure N-(4-ethyl-benzenesulfonyl)erythromycylamine was obtained. The recovered product was found to have the following values:

M. P. 138°–140°C

Analysis for $C_{45}H_{78}N_2O_{14}S$: Calculated S 3.55%; Found S 3.02%

$[\alpha]_D^{20} = -35.92°$ (1% in $CHCl_3$)

EXAMPLE 9

N-(4-propionylamino-benzenesulfonyl)erythromycylamine

A solution of 1.23 grams (0.00490 mole) p-propionylamino-benzene-sulfonylchloride in 30 ml acetone and 1.50 grams (0.01416 mole) of sodium carbonate in 40 ml water were added dropwise to a solution of 3 grams (0.00408 mole) erythromycylamine in 90 ml benzene under stirring over a period of one hour at room temperature. After this addition was completed, the reaction mixture was heated on a water bath to 50°C, stirred for one hour, cooled to room temperature (pH of the reaction mixture being 10.0), the two layers which formed were separated and the benzene layer was washed 3 times with 30 ml portions of water and dried with calcium chloride. Benzene was removed and pure N-(4-propionylamino-benzenesulfonyl)erythromycylamine was obtained. The recovered product was found to have the following values:

M. P. 173°–178°C

Analysis for $C_{46}H_{79}N_3O_{15}S$: Calculated S 3.39%; Found S 3.42%

$[\alpha]_D^{20} = -26.88°$ (1% in $CHCl_3$)

EXAMPLE 10

N-(2-methyl-benzenesulfonyl)erythromycylamine

The procedure of Example 1 was repeated, using o-toluene sulfonylchloride instead of p-toluene sulfonylchloride as starting material. The recovered product was found to have the following values:

Analysis for $C_{44}H_{76}N_2O_{14}S$; Calculated S 3.61%; Found S 3.33%

$[\alpha]_D^{20} = -38.91°$ (1% in $CHCl_3$)

What we claim is:

1. The compound N-(4-R-benzenesulfonyl)-erythromycylamine, wherein R is a lower alkyl group having 1–5 carbon atoms, an acylamino group wherein the acyl has 2–4 carbon atoms, or a halo group.

2. The compound of claim 1, wherein R is a halo group and halo represents a chlorine atom.

3. The compound of claim 1, wherein R is a halo group and halo represents a bromine atom.

4. The compound of claim 1, wherein R is a halo group and halo represents an iodine atom.

5. The compound of claim 1, wherein R is a halo group and halo represents a fluorine atom.

6. The compound of claim 1, wherein R is the lower alkyl group.

7. The compound of claim 1, wherein R is the acylamino group.

* * * * *